United States Patent
Fuchs et al.

(10) Patent No.: US 6,218,535 B1
(45) Date of Patent: Apr. 17, 2001

(54) CAPROLACTAM PRODUCTION PROCESS

(75) Inventors: Eberhard Fuchs, Frankenthal; Klemens Flick, Herxheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/486,642

(22) PCT Filed: Aug. 21, 1998

(86) PCT No.: PCT/EP98/05336

§ 371 Date: Feb. 29, 2000

§ 102(e) Date: Feb. 29, 2000

(87) PCT Pub. No.: WO99/11614

PCT Pub. Date: Mar. 11, 1999

(30) Foreign Application Priority Data

Sep. 3, 1997 (DE) .............................................. 197 38 463

(51) Int. Cl.⁷ ................................................. C07D 201/08

(52) U.S. Cl. .............................................................. 540/539

(58) Field of Search ............................................... 540/539

(56) References Cited

U.S. PATENT DOCUMENTS

| 4,568,736 | 2/1986 | Curatolo et al. | 528/313 |
| 5,495,016 | 2/1996 | Achhammer et al. | 540/539 |
| 5,646,277 | 7/1997 | Fuchs et al. | 540/539 |
| 5,739,324 | * 4/1998 | Fuchs et al. | 540/539 |

FOREIGN PATENT DOCUMENTS

| 2211015 | 8/1996 | (CA) . |
| 195 17 823 | 11/1960 | (DE) . |
| 43 39 648 | 5/1995 | (DE) . |
| 150 295 | 8/1985 | (EP) . |
| 96/22974 | 8/1996 | (WO) . |

* cited by examiner

*Primary Examiner*—Bruck Kifle
(74) *Attorney, Agent, or Firm*—Keil & Weinkauf

(57) ABSTRACT

Cyclic lactams are prepared by reacting aminocarbonitriles with water in the liquid phase in a fixed bed reactor in the presence of a catalyst which comprises a catalytically active oxide, which has no soluble constituents under the reaction conditions and which consists of shaped articles obtainable by shaping the oxide into shaped articles and, before or after said shaping, treating the oxide with from 0.1 to 30% by weight, based on the oxide, of an acid in which the oxide is sparingly soluble.

9 Claims, No Drawings

CAPROLACTAM PRODUCTION PROCESS

The present invention relates to a novel process for preparing cyclic lactams by reacting aminocarbonitriles with water in the presence of catalysts.

U.S. Pat. No. 5,646,277 discloses a process for preparing cyclic lactams by reacting aminocarbonitriles with water in the liquid phase in a fixed bed reactor in the presence of catalysts having no soluble constituents under the reaction conditions. The catalysts, which can comprise a multiplicity of oxides, selenides, tellurides and phosphates, are obtainable, for example, by extruding powders of the corresponding compounds.

It is true that this process affords cyclic lactams, but selectivity and yield are not fully satisfactory, especially at short residence times which make a high space-time yield possible and so make it possible to make the reactors smaller.

It is an object of the present invention to provide a process for preparing cyclic lactams by reacting aminocarbonitriles with water in the liquid phase in a fixed bed reactor in the presence of catalysts having no soluble constituents under the reaction conditions without the above-described disadvantages.

We have found that this object is achieved according to the present invention when the catalyst consists of shaped articles obtainable by shaping the oxide into shaped articles and, before or after said shaping, treating the oxide with from 0.1 to 30% by weight, based on the oxide, of an acid in which the oxide is sparingly soluble.

Preferred embodiments of the process of the present invention are revealed in the subclaims.

The starting materials used in the process of the present invention are aminocarbonitriles, preferably those of the general formula I

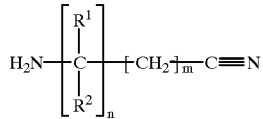
(I)

where n and m are each 0, 1, 2, 3, 4, 5, 6, 7, 8 or 9 and n+m totals at least 3, preferably at least 4.

$R^1$ and $R^2$ can in principle be substituents of any type. It is merely necessary to ensure that the desired cyclization reaction is not affected by the substituents. Preferably, $R^1$ and $R^2$ are independently $C_1$–$C_6$-alkyl or $C_5$–$C_7$-cycloalkyl or $C_6$–$C_{12}$-aryl.

Particularly preferred starting compounds are aminocarbonitriles of the general formula

where m is 3, 4, 5 or 6, especially 5. When m=5, the starting compound is 6-aminocapronitrile.

In the process of the present invention, the above-described aminocarbonitriles are reacted with water in the liquid phase using heterogeneous catalysts to form cyclic lactams. Use of aminocarbonitriles of the formula I results in the corresponding cyclic lactams of the formula II

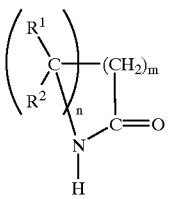

where n, m, $R^1$ and $R^2$ are each as defined above. Particularly preferred lactams are those where n is 0 and m is 4, 5 or 6, especially 5 (caprolactam being obtained in the latter case).

The reaction is carried out in the liquid phase at generally from 140 to 320° C., preferably at from 160 to 280° C.; the pressure is generally within the range from 1 to 250 bar, preferably from 5 to 150 bar, it being necessary to ensure that the reaction mixture is predominantly liquid under the conditions employed. The residence times are generally within the range from 1 to 120, preferably 1 to 90, and especially 1 to 60, min. In some cases, residence times of from 1 to 10 min have proven to be completely adequate.

The amount of water used per mole of aminocarbonitrile is generally at least 0.01 mol, preferably within the range from 0.1 to 20 mol, especially within the range from 1 to 5 mol.

The aminocarbonitrile is advantageously used in the form of a from 1 to 50% strength by weight, especially from 5 to 50% strength by weight, particularly preferably from 5 to 30% strength by weight, solution in water (in which case the solvent is also reactant) or in water/solvent mixtures. Examples of usable solvents are alkanols such as methanol, ethanol, n- and i-propanol, n-, i- and t-butanol and polyols such as diethylene glycol and tetraethylene glycol, hydrocarbons such as petroleum ether, benzene, toluene, xylene, lactams such as pyrrolidone or caprolactam, or alkyl-substituted lactams such as N-methylpyrrolidone, N-methylcaprolactam or N-ethylcaprolactam, and also carboxylic esters, preferably of carboxylic acids having from 1 to 8 carbon atoms. Ammonia can also be present in the reaction. Mixtures of organic solvents can also be used. Mixtures of water and alkanols in a water/alkanol weight ratio of 1–75/25–99, preferably 1–50/50–99, have been found to be particularly advantageous in some cases.

It is in principle equally possible to use the aminocarbonitriles as solvent as well as reactant.

The catalytically active oxides used can be, for example, acidic, amphoteric or basic oxides, preferably aluminum oxide, such as alpha- or gamma-alumina, tin oxide, zinc oxide, cerium oxide, especially titanium dioxide, amorphous, as anatase or rutile, and also their mixtures and mixed phases.

The aforementioned compounds can be doped with, or comprise, compounds of main groups 1 to 7, especially 2, 3 or 4, of the periodic table, of transition groups 1 to 7 of the periodic table, of the elements of the iron group or of the lanthanides or actinides and also mixtures thereof.

If desired, these catalysts may comprise up to 50% by weight in each case of copper, tin, zinc, manganese, iron, cobalt, nickel, ruthenium, palladium, platinum, silver or rhodium.

These catalytically active oxides are preparable in a conventional manner, for example by hydrolysis of the corresponding organics, alkoxides, salts with organic or inorganic acids and subsequent heating or calcining and also advantageously, especially in the case of titanium dioxide, pyrogenically and are generally commercially available.

According to the invention, the oxides are treated with an acid before or after shaping. Suitable acids include organic acids such as acetic acid, oxalic acid, propionic acid, butyric acid, maleic acid or inorganic acids such as isopolyacids, heteropolyacids, sulfuric acid or hydrochloric acid. Particularly suitable catalysts are obtainable by treatment with acetic acid, formic acid, nitric acid, especially phosphoric acid or polyphosphoric acid.

It is also possible to use mixtures of acids.

The treatment can be carried out continuously or batchwise in one or more stages. The individual stages can be carried out with the same acid, different acids or identical or different mixtures of acids.

Similarly, the oxides can be treated with an acid in the form mentioned before and after shaping.

Preferably, the oxides are treated with an acid before shaping.

The amount of acid used according to the invention is from 0.1 to 30%, preferably from 0.1 to 10%, especially from 0.1 to 5%, by weight, reckoned as pure acid, based on pyrogenic titanium dioxide. The acid can be mixed with a liquid diluent, such as water.

The catalysts can be prepared from the oxides without additives. It is similarly possible to add additives such as binders, for example titanium dioxide sols, salts of the oxides used, soluble titanium salt compounds, hydrolyzable titanium compounds such as titanium alkoxides or aluminum salts, such as pore-formers, for example methylcellulose, carbon fibers, fibers of organic polymers, melamine, starch powder, preferably before shaping.

The shaped articles can be present in various forms, for example as ball, tablet, cylinder, hollow cylinder, pellet, chip or strand. Such shaped articles are preparable in a conventional manner using appropriate shaping machines such as tableting machines, extruders, rotary granulators, pelletizers or combinations thereof.

The shaped material, if desired after an acid treatment, is advantageously dried, especially at from 20 to 120° C., preferably in an inert gas atmosphere or in the air, and then calcined, especially at 400–750° C., preferably in an inert gas atmosphere or in the air.

The heterogeneous catalysts are arranged in a fixed bed. The reaction can take place in a conventional manner, for example in a downflow or preferably upflow mode, especially continuously, by bringing the reaction mixture into contact with the catalyst bed.

The advantage of the process of the present invention is the possibility to operate the cyclization continuously in a simple manner with very high throughputs and high yields and selectivities and short residence times. Since the catalysts used have a long lifetime from observations to date, the result is an extremely low catalyst consumption.

EXAMPLE 1

Preparation of Pyrogenic Titanium Dioxide Extrudates (Formic Acid)

8350 g of pyrogenic titanium dioxide powder having a rutile/anatase ratio of 80/20 were kneaded for 3 hours with 47 g of 85% strength formic acid and 3750 g of water and thereafter molded into 4 mm extrudates under a molding pressure of 70 bar. The extrudates were dried at 120° C. for 16 hours and then calcined at 500° C. for 3 hours.

Analysis of extrudates:

| | |
|---|---|
| Density | 989 g/l |
| Water regain | 0.31 ml/g |
| Cutting hardness | 25 N |
| Surface area | 37 m$^2$/g |

EXAMPLE 2

Preparation of Pyrogenic Titanium Dioxide Extrudates (Phosphoric Acid)

1950 g of precipitated titanium dioxide powder (anatase) were kneaded for 3 hours with 60 g of concentrated phosphoric acid and 900 g of water and then molded into 1.5 mm extrudates under a molding pressure of 70 bar. The extrudates were dried at 120° C. for 6 hours and then calcined at 350° C. for 5 hours.

Analysis of extrudates:

| | |
|---|---|
| Density | 722 g/l |
| Water regain | 0.46 ml/g |
| Surface area | 204 m$^2$/g |

EXAMPLE 3

Preparation of Precipitated Titanium Dioxide Extrudates (Nitric Acid)

11,000 g of precipitated titanium dioxide powder (anatase) were kneaded for 2 hours with 420 g of concentrated nitric acid and 3650 g of water and then molded into 3 mm extrudates under a molding pressure of 70 bar. The extrudates were dried at 120° C. for 6 hours and then calcined at 320° C. for 2 hours and at 350° C. for a further 3 hours.

Analysis of extrudates:

| | |
|---|---|
| Density | 919 g/l |
| Water regain | 0.32 ml/g |
| Cutting hardness | 25 N |
| Surface area | 105 m$^2$/g |

EXAMPLES 4 TO 16

Conversion of 6-Aminocapronitrile into Caprolactam

A solution of 6-aminocapronitrile (ACN) in water and ethanol in the weight ratios reported in the table was passed into a 25 ml capacity heated tubular reactor (diameter 6 mm; length 800 mm) packed with catalysts 1 to 4 recited in the table, in the form of granules. The product stream leaving the reactor was analyzed by gas chromatography. The results are recited in the table as examples.

As well as caprolactam, the product stream comprises essentially ethyl ε-aminocaproate and ε-aminocaproamide. Both can likewise be cyclized to form caprolactam. In addition, the stream includes from 5 to 8% of caprolactam oligomer which can be cracked to form caprolactam monomer.

TABLE

| Ex. | Catalyst | ACN [% by wt.] | Water [% by wt.] | Molar ratio ACN/H$_2$O [%] | Ethanol [% by wt.] | Temp. [°C.] | Residence time [min] | ACN conversion [%] | Capro selectivity [%] |
|---|---|---|---|---|---|---|---|---|---|
| 4 | 1 | 10 | 3.2 | 2 | 86.8 | 230 | 21 | 99 | 89 |
| 5 | 1 | 10 | 3.2 | 2 | 86.8 | 230 | 8 | 99 | 92 |
| 6 | 1 | 10 | 3.2 | 2 | 86.8 | 230 | 5 | 99 | 88 |
| 7 | 2 | 10 | 3.2 | 2 | 86.8 | 180 | 30 | 93 | 93 |
| 8 | 2 | 10 | 6.4 | 4 | 83.6 | 180 | 30 | 92 | 92 |
| 9 | 2 | 10 | 3.2 | 2 | 86.8 | 230 | 10 | 100 | 93 |
| 10 | 2 | 10 | 6.4 | 4 | 83.6 | 230 | 10 | 100 | 91 |
| 11 | 3 | 10 | 3.2 | 2 | 86.8 | 230 | 22 | 99 | 88 |
| 12 | 3 | 10 | 3.2 | 2 | 86.8 | 230 | 9 | 99 | 92 |
| 13 | 3 | 10 | 3.2 | 2 | 86.8 | 230 | 5 | 96 | 90 |
| 14 | 4 | 10 | 3.2 | 2 | 86.8 | 230 | 20 | 100 | 91 |
| 15 | 4 | 10 | 3.2 | 2 | 86.8 | 230 | 8 | 96 | 92 |
| 16 | 4 | 10 | 3.2 | 2 | 86.8 | 230 | 5 | 87 | 90 |

Catalysts 1 to 4 were prepared similarly to catalyst examples 1 to 3:

Catalyst 1: Precipitated titanium dioxide extruded with 3% of phosphoric acid as 3 mm extrudates and then ground to granules 1.0–1.5 mm in size Catalyst 2: Precipitated titanium dioxide extruded with 3% of phosphoric acid as 3 mm extrudates Catalyst 3: Pyrogenic titanium dioxide extruded with 3% of phosphoric acid as 4 mm extrudates and then ground to granules 1.6–2.0 mm in size Catalyst 4: Pyrogenic titanium dioxide extruded with 0.5% of formic acid as 4 mm extrudates and then ground to granules 1.6–2.0 mm in size

We claim:

1. The process for preparing cyclic lactams by reacting aminocarbonitriles with water in the liquid phase in a fixed bed reactor in the presence of a catalyst which comprises a catalytically active oxide, which has no soluble constituents under the reaction conditions and which consists of shaped articles obtainable by shaping the oxide into shaped articles and, before or after said shaping, treating the oxide with from 0.1 to 30% by weight, based on the oxide, of an acid in which the oxide is sparingly soluble.

2. The process of claim 1, wherein the reaction is carried out at a temperature within the range from 140 to 320° C.

3. The process of claim 1, wherein the aminocarbonitriles used have the formula

$$H_2N\text{—}(CH_2)_m\text{—}C\equiv N$$

where m is 3, 4, 5 or 6.

4. The process of claim 3, wherein the aminocarbonitrile used is 6-aminocapronitrile.

5. The process of claim 1, wherein the aminocarbonitrile is used in the form of a from 1 to 50% strength by weight solution in water or in water/org. solvent mixtures.

6. The process of claim 1, wherein the catalytically active oxide is titanium dioxide, aluminum oxide, tin oxide, zinc oxide, cerium oxide or a mixture thereof.

7. The process of claim 1, wherein the acid used is phosphoric acid or polyphosphoric acid.

8. The process of claim 1, wherein the acid used is nitric acid, acetic acid or formic acid.

9. The process of claim 1 wherein the oxides are present in the shape of balls, tablets, cylinders, hollow cylinders, pellets, chips or strands.

* * * * *